US007094560B2

(12) United States Patent
Brown et al.

(10) Patent No.: US 7,094,560 B2
(45) Date of Patent: Aug. 22, 2006

(54) STABILIZATION OF T4 ENDONUCLEASE V

(75) Inventors: Anne B. Brown, Merrick, NY (US); David A. Brown, Merrick, NY (US); Daniel B. Yarosh, Merrick, NY (US)

(73) Assignee: Applied Genetics Incorporated Dermatics, Freeport, NY (US)

( * ) Notice: Subject to any disclaimer, the term of this patent is extended or adjusted under 35 U.S.C. 154(b) by 0 days.

(21) Appl. No.: 10/490,397

(22) PCT Filed: Sep. 20, 2002

(86) PCT No.: PCT/US02/29885

§ 371 (c)(1),
(2), (4) Date: Mar. 23, 2004

(87) PCT Pub. No.: WO03/027238

PCT Pub. Date: Apr. 3, 2003

(65) Prior Publication Data

US 2004/0248230 A1    Dec. 9, 2004

Related U.S. Application Data

(60) Provisional application No. 60/324,448, filed on Sep. 24, 2001.

(51) Int. Cl.
*C12Q 1/37* (2006.01)
*C12N 9/22* (2006.01)

(52) U.S. Cl. .......................................... 435/23; 435/199
(58) Field of Classification Search ............... 435/23, 435/199
See application file for complete search history.

(56) References Cited

U.S. PATENT DOCUMENTS

| 5,077,211 | A |   | 12/1991 | Yarosh |
|---|---|---|---|---|
| 5,141,852 | A |   | 8/1992 | Egan et al. |
| 5,190,762 | A |   | 3/1993 | Yarosh |
| 5,272,079 | A | * | 12/1993 | Yarosh .................. 435/193 |
| 5,296,231 | A |   | 3/1994 | Yarosh |
| 5,302,389 | A |   | 4/1994 | Kripke et al. |
| 5,352,458 | A |   | 10/1994 | Yarosh |
| 5,580,747 | A | * | 12/1996 | Shultz et al. .................. 435/24 |
| 5,945,033 | A |   | 8/1999 | Yen |

OTHER PUBLICATIONS

Yarosh, D.B., et al. (1999) Photochem. Photobiol. 69(2), 136-140.*
Dodson, M.L., et al. (1991) Mutation Res. 255, 19-29.*
Carrier et al., "Endonuclease from *Micrococcus luteus* that has activity toward ultraviolet-irradiated deoxyribonucleic acid: purification and properties," *Journal of Bacteriology* (1970), 102:178-186.
Friedberg et al., "Dark repair of ultraviolet-irradiated deoxyribonucleic acid by bacteriophage T4: purification and characterization of a dimer-specific phage-induced endonuclease," *Journal of Bacteriology* (1971), 106:500-507.
Higgins et al., "Purification of the T4 endonuclease V," *Mutation Research* (1987), 183:117-121.
Nakabeppu et al., "Physical association of pyrimidine dimer DNA glycosylase and apurinic/apyrimidinic DNA endonuclease essential for repair of ultraviolet-damaged DNA," *Proceedings of the National Academy of Sciences* (1981), 78:2742-2746.
Seawell, et al., "Purification of endonuclease V of bacteriophage T4" in *DNA Repair: A Laboratory Manual of Research Procedures*, vol. 1A, 1981, Marcel Dekker (New York). 229-236.
White et al., "PepTag™ Protease Assay: A Simple and Rapid Method for the Detection of Very Low Amounts of Protease," *Promega Notes Magazine* (1993), 44:2-7.
Yasuda et al., "T4 endonuclease involved in repair of DNA," *Proceedings of the National Academy of Sciences* (1970), 67:1839-1845.
Yasuda et al., "Further purification and characterization of T4 endonuclease V," *Biochimica et Biophysica Acta* (1976), 442:197-207.
Promega Corporation's Technical Bullentin No. 185 entitled "PepTag™ Protease Assay," Madison, Wisconsin, Nov. 1994, pp. 1-8.

* cited by examiner

*Primary Examiner*—Charles L. Patterson, Jr.
(74) *Attorney, Agent, or Firm*—Maurice M. Klee

(57) ABSTRACT

The invention provides T4 endonuclease V compositions that exhibit enhanced stability, including stability at non-refrigerated temperatures, through reduced activity of cryptic proteases. Methods for detecting cryptic protease activity and methods for reducing such activity are also provided.

10 Claims, 8 Drawing Sheets

STABILIZATION OF T4 ENDONUCLEASE V

CROSS REFERENCE TO RELATED APPLICATIONS

This application is the U.S. national phase under 35 USC §371 of International Application No. PCT/US02/29885, filed Sep. 20, 2002, which was published in English under PCT Article 21(2) on Apr. 3, 2003 as International Publication No. WO 03/027238. This application claims the benefit under 35 USC §119(e) of U.S. Provisional Application No. 60/324,448 filed Sep. 24, 2001.

FIELD OF THE INVENTION

The present invention relates to preparations of the enzyme T4 endonuclease V that are stable during storage at temperatures above refrigeration.

As defined by the U.S. Pharmacopoeia Section 24, "cold" is "any temperature not exceeding 8° C. (46° F.)" and a "refrigerator is a cold place in which the temperature is maintained thermostatically between 2° and 8° C. (36° and 46° F.)." Accordingly, as used herein, "refrigeration" refers to temperatures up to 8° C. (46° F.).

As known in the art, T4 endonuclease V (referred to herein as "T4 endo V") is useful in medicine, health maintenance, and for other purposes. Its use, however, has been limited by its instability when stored at temperatures above refrigeration. The present invention describes methods for providing T4 endo V with stability at temperatures above refrigeration. The invention also provides (1) assay methods for use in achieving this stability and (2) T4 endo V compositions which exhibit such stability.

DESCRIPTION OF RELATED ART

U.S. Pat. No. 5,077,211 and U.S. Pat. No. 5,272,079, both entitled "Purification and Administration of DNA Repair Enzymes", relate to methods for purifying DNA repair enzymes and encapsulating them in liposomes for topical delivery.

U.S. Pat. No. 5,296,231, "Purification and Administration of DNA Repair Enzymes", relates to methods for purifying DNA repair enzymes and encapsulating them in liposomes sensitive to changes in pH for purposes of topical delivery.

U.S. Pat. No. 5,190,762, "Method of Administering Proteins to Living Skin Cells", relates to the application of biologically active proteins, including enzymes, in liposomes into cells of the skin.

U.S. Pat. No. 5,302,389, "Method for Treating UV-Induced Suppression of Contact Hypersensitivity by Administration of T4 Endonuclease", relates to the use of DNA repair liposomes encapsulating T4 endo V to protect the immune system.

U.S. Pat. No. 5,352,458, "Tanning Method Using DNA Repair Liposomes", relates to the use of DNA repair liposomes to increase the tanning response.

Carrier, W. L. and R. B. Setlow. Endonuclease from *Micrococcus luteus* that has activity toward ultraviolet-irradiated deoxyribonucleic acid: purification and properties. *Journal of Bacteriology* (1970), volume 102, pp. 178–186. Purification of an enzyme similar to T4 endonuclease V from *M. luteus* is described. The enzyme is unstable and sensitive to freezing (p 180): "The purified activity is stable for several weeks at 4° C. It loses 50% of its activity on freezing and is very unstable at higher temperatures. For example, it loses all its activity in 30 min at 37° C." The stability can be increased by addition of calf thymus DNA.

Dodson, M., M. Prince, W. Anderson and R. Lloyd (1991) Site-directed deletion mutagenesis within the T4 endonuclease V gene: dispensable sequences within putative loop regions. *Mutation Research* 255:19–29. Studies on the importance of specific sites in the T4 endonuclease V protein reveal loop regions that are essential for proper folding and functioning of the enzyme.

Friedberg, E. C. and J. J. King (1971) Dark repair of ultraviolet-irradiated deoxyribonucleic acid by bacteriophage T4: purification and characterization of a dimer-specific phage-induced endonuclease. *Journal of Bacteriology* (1971) Volume 106, pp. 500–507. A method for purification of T4 endonuclease V is described. The resulting enzyme is labile and storage with calf thymus DNA at 4° C. is recommended. The final fractions "are unstable when frozen and are stored at 3C in the presence of either 3% polyethylene glycol or DNA (20 ug/ml). About 80% of the activity is lost by heating the enzyme to 45C for 10 min." (page 502)

Higgins, K. M. and R. S. Lloyd. Purification of the T4 endonuclease V. *Mutation Research*, (1987) volume 183, pp. 117–121. A method for purification of T4 endonuclease V is described. All procedures are recommended to be performed at 0–4° C. unless otherwise noted. No recommendation on storage is noted.

Nakabeppu, Y. and M. Sekiguchi. Physical association of pyrimidine dimer DNA glycosylase and apurinic/apyrimidinic DNA endonuclease essential for repair of ultraviolet-damaged DNA. *Proceedings of the National Academy of Sciences* (1981) volume 78, pp. 2742–2746. The purified T4 endo V contains both a dimer specific glycosylase activity and an AP endonuclease activity on the same polypeptide. The AP DNA endonuclease activity was destroyed at 42° C. very rapidly, within 5 minutes, while the glycosylase activity was lost at a rate of 4% per minute at this temperature.

Seawell, P. C., E. C. Friedberg, A. K. Ganesan, P. C. Hanawalt. Purification of endonuclease V of bacteriophage T4, in *DNA Repair: A Laboratory Manual of Research Procedures*, vol 1A, 1981. Marcel Dekker (New York). Chapter 19: Purification of Endonuclease V of bacteriophage T4. pp. 229–236. A method for purification of T4 endonuclease V is described. All purification methods are recommended to be performed at 0° C. The purified enzyme is not recommended to be stored at room temperature (p 235): "The dialyzed phosphocellulose fraction can be stored for several months at 4° C., but is inactivated by freezing. Further purification of T4 endonuclease by several procedures has been reported; however, in our experience, extensively purified enzyme is labile to storage."

Yarosh, D., A. O'Connor, L. Alas, C. Potten, P. Wolf. Photoprotection by topical DNA repair enzymes: Molecular correlates of clinical studies. *Photochemistry and Photobiology*. (1999) 69:136–140. Inactivation of the T4 endo V was measured in some lots at 10° C., 25° C. and 37° C. The enzyme is shown to recover activity under certain conditions after SDS denaturation as well as heat denaturation. The hypothesis is presented that the lability of T4 endonuclease V is due to the ease of protein unfolding at the hinge regions between the helices.

Yasuda, S. and M. Sekiguchi. T4 endonuclease involved in repair of DNA. *Proceedings of the National Academy of Sciences* (1970) volume 67, pp. 1839–1845. This is the first description of the purification of T4 endo V and the paper in which the enzyme is named. No recommendation for storage of the enzyme is provided.

Yasuda, S. and M. Sekiguchi. Further purification and characterization of T4 endonuclease V. *Biochimica et Biophysica Acta* (1976) volume 442, pp. 197–207. A method for purification of T4 endonuclease V is described. All procedures are recommended to be carried out at 0–4° C. The preparation used in most of the experiments was stored at 0° C. (page 202). The enzyme is noted to be labile: "Although endonuclease V is relatively stable when stored at 0° C. it is extremely heat labile and loses 80% of its activity within 8 minutes of preincubation at 40° C." (page 203–204)

Stability of T4 Endo V Purified by Prior Art Methods

As mentioned above, a significant impediment to the widespread use of T4 endo V is the current limitation on its storage at temperatures greater than refrigeration. Many methods have been used to purify T4 endo V, including the methods described in the references referred to above. Some of these methods have included the use of metal chelators such as EDTA and/or ion-exchange chromatography. However, commercial application of these methods, e.g., application of the methods to fermentations and purifications of 200 liters or more, yield products that are not stable for periods of a week or longer unless stored at refrigeration or frozen.

Stability studies presented in the literature demonstrate a short half-life for T4 endo V at temperatures greater than refrigeration. Commercial suppliers of T4 endo V, such as EPICENTRE of Madison, Wis. always ship their enzymes under refrigerated or frozen conditions, despite the additional costs, and recommend storage under frozen conditions.

Work at Applied Genetics Incorporated Dermatics, the assignee of this application, also showed that preparations of purified T4 endo V showed inconsistent and limited stability. In surveying many lots we noticed a wide variation in enzyme stability, from extreme to moderate instability. For commercial size batches, we found an average activity half-life of 6 months under refrigerated conditions and at room temperature, the average activity half-life was about 3 months. We often found in some lots that enzyme activity disappeared in less than a week incubation at greater than refrigeration temperatures. The inconsistency in stability is a significant hindrance to commercial use of the enzyme. In the above paper in *Photochemistry and Photobiology*, we proposed that the instability of the enzyme was due to denaturation of the protein, and we were supported in this view by the report by Dodson et al. in *Mutation Research*, 1991, (see above) who stated that correct folding of loop regions within the protein were particularly essential to enzyme stability.

SUMMARY OF THE INVENTION

The present invention provides a composition of T4 endo V that can be stored at greater than refrigerated temperature (e.g., at room temperature). This is accomplished by removal of cryptic (trace) proteases and/or the inhibition of such protease activity.

In another aspect, the present invention provides a method for storing T4 endo V at greater than refrigerated temperature by including in the composition protease inhibitors, deflectors of protease activity, or decoys for protease activity.

In yet another aspect of the invention, T4 endo V that can be stored at greater than refrigerated temperatures is produced by removing proteases during enzyme manufacturing or by including in the manufacturing process protease-specific proteases, suicide inhibitors of proteases and/or chemical inactivators of proteases in amounts sufficient to eliminate the trace protease activity that remains after standard purification.

The present invention further provides a method for detecting trace protease activity not otherwise detected by extending the time in which an indicator protease substrate (reporter peptide) is in contact with a test sample.

In accordance with a first of its method aspects, the invention provides a method for detecting protease contaminants in a T4 endonuclease V composition (e.g., an intermediate composition in an overall manufacturing process or a final commercial composition) comprising:

(i) preparing a test solution comprising an aqueous buffer (e.g., a Tris-HCl, pH 8 buffer), a sample of the T4 endonuclease V composition, and a reporter peptide;

(ii) incubating (under standard laboratory conditions) the test solution at 25° C. for a period of at least 7 days; and (iii) determining the degradation of the reporter peptide after step (ii).

The preferred embodiments of the first method aspect of the invention are characterized by:

(1) the concentration of the T4 endonuclease V in the test solution is 0.095±0.05 mg/ml, (2) the reporter peptide is a labeled reporter peptide whose amino acid sequence is Pro Leu Ser Arg Thr Leu Ser Val Ala Ala Lys (i.e., the C1 reporter peptide of the commercial PROMEGA PEPTAG™ kit (PROMEGA Corporation (Madison, Wis.)); see SEQ ID NO: 1), and/or (3) step (iii) is performed by subjecting at least a portion of the test solution to a peptide separation procedure (e.g., agarose gel electrophoresis) and determining the percentage of degradation of the reporter peptide by densitometry (e.g., a computer analysis of a digitized fluorescent image of the gel for a reporter peptide having a fluorescent label).

In addition to the sample(s) of the T4 endonuclease V composition(s) being tested, in conformance with standard laboratory procedures, positive and negative controls are preferably also tested. The positive control will contain a protease known to degrade the labeled reporter peptide used in the test, while the negative control can be, for example, the buffer and the labeled reporter peptide with no sample of the composition.

As is conventional in biological assays, e.g., assays for enzyme activity, the concentration of the reporter peptide in the test solution of step (i) is selected so that the protease activity of the positive control can be reliably detected. For example, for the preferred C1 reporter peptide of SEQ ID NO: 1, suitable reporter peptide concentrations in the test solution include 0.03 mg/ml, 0.04 mg/ml, 0.06 mg/ml, and 0.095 mg/ml, each of which will reliably detect protease activity in a positive control, such as, the alkaline protease positive control recommended for use with the PROMEGA PEPTAG™ kit. See Promega Corporation's Technical Bulletin No. 185 entitled "PepTag™ Protease Assay," Madison, Wis., November 1994, pages 1–8. Other reporter peptide concentrations can, of course, be used in the practice of the invention, e.g., any concentration in, for example, the 0.03 to 0.095 mg/ml range or the 0.04 to 0.06 mg/ml range, provided the concentration is sufficiently high to reliably detect the presence of proteases in a positive control under the particular assay conditions employed. Preferably, as illustrated by the examples presented below, the reporter peptide/positive control/negative control combination results in 100% degradation of the reporter peptide by the positive control and 0% degradation by the negative control under the assay conditions employed. To ensure a reliable/valid assay, as a general rule, the concentration of the reporter peptide in the test solution should be greater than 0.03 mg/ml.

In accordance with a second of its method aspects, the invention provides a method for preparing a T4 endonuclease V composition (e.g., an intermediate composition in an overall manufacturing process or a final commercial composition) comprising:

(A) providing an aqueous solution containing T4 endonuclease V (again, the aqueous solution can be an intermediate or final solution); and (B) treating the aqueous solution so as to reduce the protease activity of the composition (e.g., through the use of a quarternary ammonium moiety attached to a solid support and/or with a chelating agent);

wherein as a result of step (B), the composition has a protease activity of less than 10 percent, where the protease activity is determined by the first method aspect of the invention employing, as discussed above, (1) the preferred T4 endonuclease V concentration, (2) the preferred reporter peptide, and (3) the preferred degradation determination technique, the percentage of degradation so determined being the protease activity.

In accordance with a first of its product aspects, the invention provides a composition comprising T4 endonuclease V wherein the composition has a protease activity of less than 10 percent, where the protease activity is determined by the first method aspect of the invention employing, as discussed above, (1) the preferred T4 endonuclease V concentration, (2) the preferred reporter peptide, and (3) the preferred degradation determination technique, the percentage of degradation so determined being the protease activity.

In accordance with a second of its product aspects, the invention provides a composition comprising T4 endonuclease V (e.g., a composition of T4 endonuclease V and a suitable carrier such as an aqueous carrier containing pharmaceutical excipients) wherein the composition retains at least 10 percent of its initial activity after storage at 25° C. for a period of six months.

BRIEF DESCRIPTION OF THE DRAWINGS

In FIG. 1, the fit of the regression line to the data of this figure has an $R^2$ value of 0.9093.

The foregoing figures, which are incorporated in and constitute part of the specification, illustrate the preferred embodiments of the invention, and together with the description, serve to explain the principles of the invention. It is to be understood, of course, that both the figures and the description are explanatory only and are not restrictive of the invention.

The "% degradation" values reported in FIGS. 2, 4–6, and 8 were obtained in the conventional manner by: (1) obtaining densitometry values for each well (each column of the gel) for (a) the intact peptide ($D_{intact}$) and (b) all fragments; (2) computing the sum of the densitometry values for the fragments ($D_{sum}$); and (3) forming the ratio $D_{sum}/(D_{sum}+D_{intact})$. Percent degradation was then $100 \cdot D_{sum}/(D_{sum}+D_{intact})$.

Figure 6:
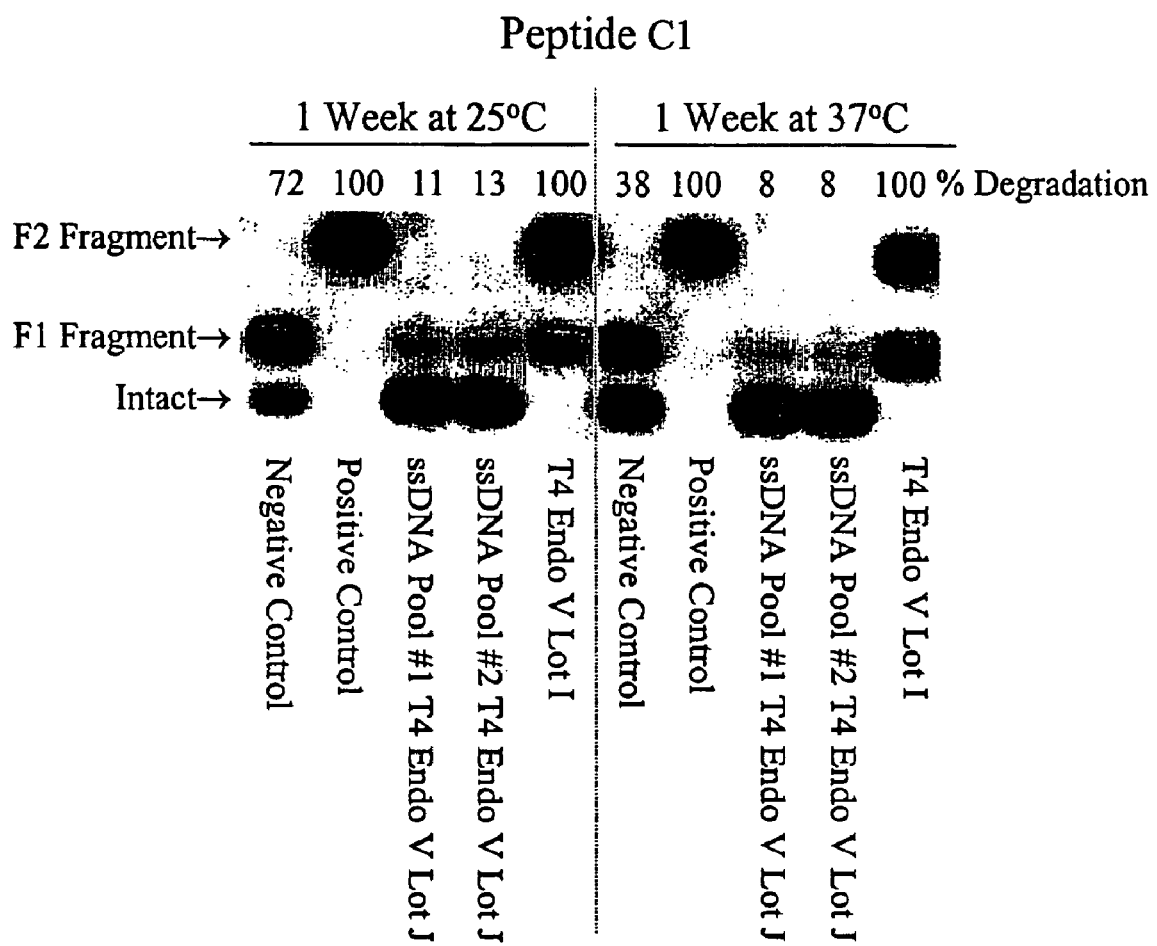
FIG. 6 shows removal of protease activity in T4 endonuclease V lots containing EDTA and passed through FFQS. T4 endonuclease V purified in the presence of 3.4 mM EDTA and passed through FFQS was assayed at 25° and 37° C. for 1 week for protease activity. The concentration of C1 peptide in the test solution was 0.04 mg/ml. Greatly reduced levels were found compared to Lot I.

The percent degradation values for samples of T4 endonuclease V compositions were then compared to the percent degradation value obtained for a negative control to confirm that the protease activities observed for samples were due to endogenous proteases and not due to contamination introduced during the experimental procedure. The value of using a negative control for this purpose is illustrated in FIG. 6 where instead of having zero percent degradation, as it should have, the negative control showed high levels of degradation (72% and 38% for the 25° C. and 37° C. incubations, respectively). These high levels of degradation were traced to the lot of water used to prepare the negative control which was found to have an elevated bacteria count and a protease activity higher than other water lots, and was therefore not used in further experiments and was discarded.

DETAILED DESCRIPTION OF THE INVENTION

As discussed above, the present invention provides T4 endo V compositions that can be stored at temperatures above refrigeration by the elimination of cryptic proteases from the compositions.

The role of such proteases and, in particular, the unusual sensitivity of T4 endo V to even the slightest amount of protease activity, was discovered by examination of plots of activity versus time during storage at 4° C. for three lots of purified T4 endonuclease V. From these plots, it was observed that not only did the initial amount of enzyme activity vary, but the stability rate also varied. This was unexpected if the stability was a characteristic of the enzyme.

Regression analysis of these plots showed that the rate of decay of the enzyme (slope) was directly proportional to the initial amount of activity (intercept). In other words, for any batch of T4 endo V, the rate of decay could be predicted from the initial level of activity. Based on this correlation, it was hypothesized that the same factor that destroyed T4 endo V activity during storage also controlled the initial activity level, and it was further hypothesized that this factor was protease activity in the T4 endo V preparation.

In order to test this hypothesis that protease activity limited the stability of T4 endo V, protease activity was assayed in lots of T4 endo V using a standard protease activity assay, namely, the PEPTAG™ assay of PROMEGA Corporation (Madison, Wis.). In this assay, peptides with fluorescent end-labels are incubated with a test sample, and then the peptides are subjected to electrophoresis. If protease activity cleaves the peptides, the migration of the end-labeled peptide is altered because it is shorter and/or changed in charge. Two test peptides of different lengths and amino acid sequences are used to detect a broader range of proteases.

Following the standard assay procedure recommended by the manufacturer, which included a 30 minute incubation of test sample with peptide, no protease activity was detected in any of nine purified T4 endo V preparations using either the A1 peptide (amino-terminus labeled) or C1 peptide (carboxy terminus-labeled). Similarly, no protease activity was detected when the incubation time was extended from 30 minutes to 18 hours with either peptide. In fact, no substantial protease activity was consistently detected when the nine preparations were incubated with the A1 peptide for either 1 or 2 weeks. However, protease activity was discovered in each of the nine T4 endo V preparations after 1 or 2-week incubations with the C1 peptide.

This discovery of an assay method to detect cryptic protease activity was an important breakthrough in understanding the inconsistent stability of T4 endo V compositions since it allowed identification of protease activity in purified preparations of enzyme that were otherwise undetectable.

The level of protease activity was then analyzed in two of the T4 endo V preparations, and compared to the stability of those preparations. The slope of the enzyme activity versus time curve was found to correlate with protease activity. In particular, the lots with the higher protease activity had the least stability, and the lots with the least protease activity had the greatest stability.

This discovery forms the basis of the present invention since it means that by measuring and then eliminating trace levels of protease activity which can act over weeks and months, the stability of T4 endo V, and the consistency of enzyme lots, can be improved. This, in turn, allows storage at temperatures greater than refrigeration, thereby increasing the commercial value of T4 endo V.

In particular, enzymes such as T4 endo V can be made more commercially useful by extending the range of the recommended storage temperature up to room temperature. Commercial standards can be from 6 months up to 3 years stability; that is, during this time, the enzyme must remain within specifications when stored at room temperature, i.e., at a temperature of up to 30° C.

In the case of T4 endo V, as discussed above and demonstrated below, this room temperature storage can be accomplished by removal of protease activity. Proteases are enzymes that degrade protein. They can be non-specific, and attack almost all proteins, or specific for certain proteins or certain peptide linkages. A species of proteases is often found in nature within a mixture of several proteases. In some cases enzymes are reported to be sensitive to cold or freezing, but this can be due to protease contaminants in the preparation that have time to act during the thawing process when such a process is performed at an elevated temperature.

Proteases are often stimulated by using divalent ions as co-factors, and therefore the chelating activity of EDTA can reduce protease activity. EDTA is generally used as an efficient chelator in biochemistry at concentrations above 0.1% and below 0.5 wt. %. EDTA may be kept in the final product or removed if desired. There are several compounds similar in structure and activity to EDTA, such as EGTA and ergothioneine. In accordance with the invention, the concentration of chelating agent must be high enough to significantly reduce cryptic protease activity, e.g., reduce such activity by at least 50%, preferably by 80%, and most preferably by 90%.

An additional method for reducing protease activity is to use molecules that disrupt or block the active site or mechanical functions of the protease. They may be specific for a protease, or broad-spectrum inhibitors. Molecules such as these include phenylmethylsulfonyl fluoride and leupeptin. The preferred protease inhibitor is non-toxic, active at low concentrations, inexpensive, and does not interfere with the activity of the T4 endo V enzyme. Such inhibitors do not remove, but rather merely inhibit, proteases, and therefore, when used, they are included in the final enzyme preparation. (Note that chelators can be removed from the final preparation because they take with them protease co-factors (e.g., divalent ions) and thus in this way reduce protease activity.) As with chelating agents, the concentration of the inhibitor must be high enough to significantly reduce cryptic protease activity, e.g., reduce such activity by at least 50%, preferably by 80%, and most preferably by 90%.

A preferred approach for reducing protease activity in T4 endo V compositions is to remove proteases through binding to quaternary ammonium groups ("Q" groups). Such removal can be accomplished by means of Q-based chromatography media, such as Q-SEPHAROSE and fast flow Q membranes. For ease of reference, the abbreviations "Q" and "Q-" are used herein to refer to all affinity binding media with anion exchange characteristics similar to quaternary ammonium moieties. These media can be used in column chromatography, batch stirring, or solid support forms.

When the chromatography conditions are selected so that the affinity of the protease for Q-binding is greater than the affinity of T4 endo V for Q-binding, then the protease-free enzyme will be found in the flow-through fractions. On the other hand, when the affinity of the protease for Q-binding is less than that of T4 endo V, then protease activity will be found in the flow-through fractions, and the T4 endo V without proteases can be eluted from the Q-binding matrix, using salt or pH or other chaotropic agents. The most desirable process is one that uses inexpensive chromatography media that is easily cleaned, and a process where T4 endo V flows through and proteases are retained. However used, Q-binding preferably significantly reduces cryptic protease activity of the T4 endo V composition, e.g., reduces such activity by at least 50%, preferably by 80%, and most preferably by 90%.

Several other methods are available for reducing or eliminating protease activity in T4 endo V compositions. Molecular chaperones are protein molecules that bind to a wide variety of enzymes and protect them from denaturation and others hazards within the cell. Chaperones or other physical protectors from proteases may be used to increase the stability of T4 endo V. The most desirable chaperones are those that are inexpensive, non-toxic, and do not inhibit the activity of T4 endo V. Decoy substrate proteins, and suicide protease substrates may be used to absorb, sequester or destroy proteases. These have the advantage of destroying the protease activity so that the proteases can be subsequently removed. The preferred decoys and suicide substrates are those that are efficient, inexpensive, non-toxic and easily removed. Again, these methods should achieve a significant reduction in protease activity, e.g., a reduction in such activity by at least 50%, preferably by 80%, and most preferably by 90%.

While neither EDTA nor Q-binding nor any other method alone may completely eliminate protease activity, the use of any of these methods or a combination thereof can result in a T4 endo V product that can be stored at temperatures above refrigeration.

The T4 endo V used in the practice of the invention may exist in an extract, or in a semi-pure or purified state prepared from feedstock that contains proteases. The enzyme may be fermented from either prokaryotic or eukaryotic cells, including plants. The final T4 endo V composition can include various components conventionally used in the pharmaceutical and cosmetic fields, such as excipients, anti-microbials, bulking agents, coloring agents, fragrances, and the like. Typically, the T4 endo V compositions of the invention will be used in topical preparations applied to humans or animals. Preferably, the T4 endo V composition will comprise liposomes in which the enzyme is encapsulated. The U.S. Patents referred to above, the relevant portions of which are incorporated herein by reference, discuss various preferred applications for the T4 endo V compositions of the present invention.

The uses of and various useful and novel features of the present invention will be further understood in view of the following non-limiting examples.

EXAMPLE 1

This example demonstrates that the relationship between T4 endo V enzyme stability and initial activity indicates the presence of protease activity, even if protease activity cannot be detected by standard assays. The relationship can be seen in a plot of three or more lots of the enzyme preparation, when the slope of the loss of enzyme activity is plotted against the initial enzyme activity.

T4 endonuclease activity was determined by preparing a substrate of plasmid pMJR1560 at 200 µg/ml irradiated with 40 J/m$^2$ of UV-C from a germicidal lamp, and mixing it with 200 µg/ml of unirradiated plasmid pSV2neo. Ten µl of this substrate was then mixed with 1 ng of each of three lots of T4 endonuclease V protein in a 50 mM Tris-HCl buffer, pH 8 and 10 mM EDTA. The lots had been purified in accordance with the procedures of U.S. Pat. No. 5,077,211. (The procedures of this patent were also used for preparation of all of the other lots referred to herein except where indicated.) After 60 min incubation at 37° C., the DNA was analyzed on a 0.8% neutral agarose gel.

The substrate migrates as two supercoiled bands, with the irradiated and smaller pMJR1560 plasmid migrating faster than the larger pSV2neo plasmid. After T4 endonuclease V acts on the UV-irradiated supercoiled plasmid pMJR1560, the resulting open circular plasmid form migrates more slowly than the pSV2neo plasmid. The percent of the total pMJR1560 plasmid that migrates in the supercoiled position is an inverse measure of T4 endonuclease V activity. One "hit" is the amount of enzyme activity that reduces the amount of supercoiled plasmid to 37%. A unit of activity is equal to the number of hits for 100 µg of substrate mixture. Specific activity is the number of units per µg of enzyme.

The three lots of T4 endonuclease V were assayed during storage at 4° C. The data were plotted as net pMJR hits (by subtracting the hits found in the unirradiated control pSV2neo plasmid) versus date. From a plot of weekly measurements in duplicate over five months, a regression line was fitted to the data. The slope was taken as the slope of the stability curve, and each regression equation was solved for the activity at the initial date of manufacturing. The slope of the stability curve was plotted against the initial activity.

Figure 1:
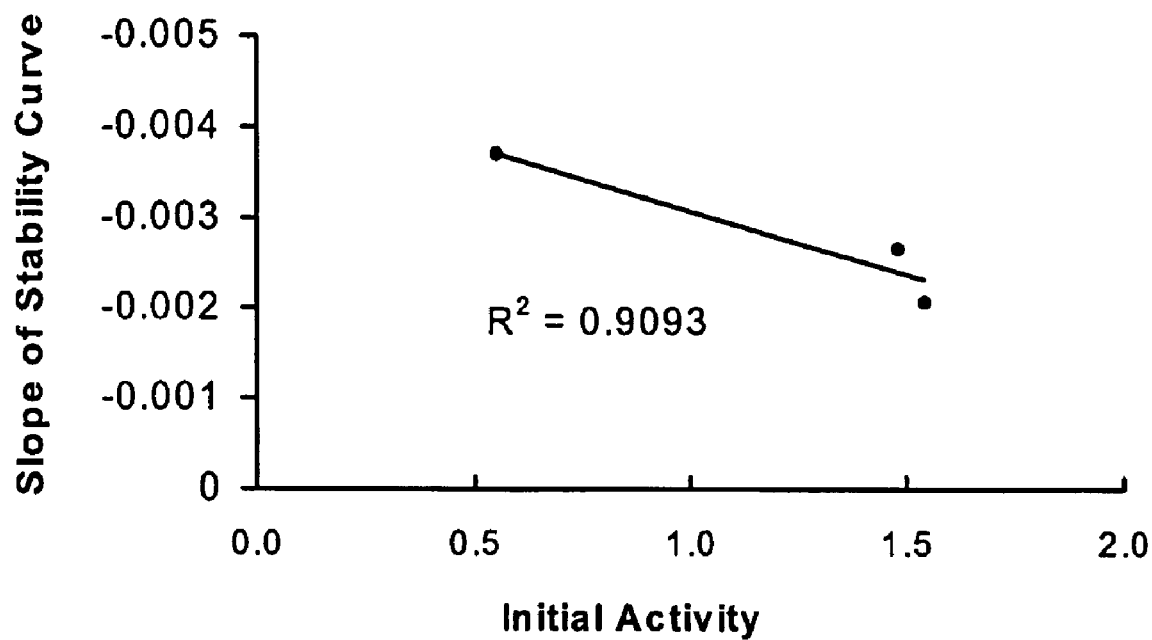
FIG. 1 shows the relation between initial activity and rate of decay of T4 endonuclease V. This graph plots the slope of the stability curve against the initial activity for three lots of T4 endonuclease V. The data was derived from stability studies, in which the slope of the stability curve is the slope of a linear regression line fitted to a plot of T4 endonuclease V activity versus time, and the initial activity is taken as the intercept obtained when the regression equation is solved for the date of manufacturing of the enzyme.

The result is shown in FIG. 1. The resulting plot shows a linear relationship between slope and initial activity with a goodness of fit of 0.9093.

EXAMPLE 2

Standard assays for protease activity, such as the PROMEGA PEPTAG™ kit, direct the user to incubate 1 µl of each of the A1 and C1 substrates with 5 µl of the sample in a 10 µl total reaction buffered with 50 mM Tris-HCl, pH 8.0, for 30 minutes at room temperature, and then to analyze the products in a 1% agarose gel. As a positive control, 2.5 µl of a 20 ng/µl solution of alkaline protease is used, i.e., 50 ng of alkaline protease.

Figure 2:
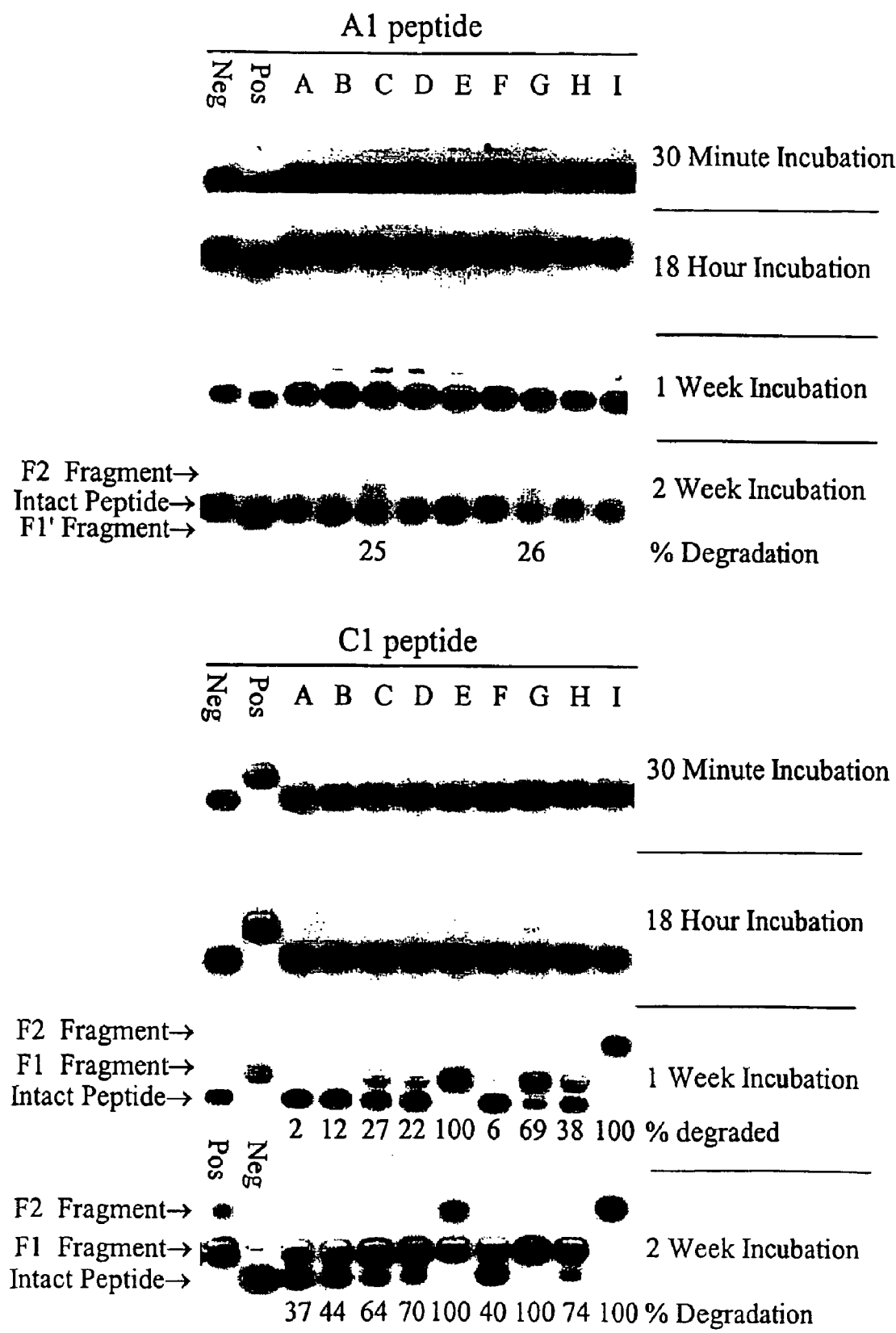
FIG. 2 shows the results of assaying protease activity in lots of purified T4 endonuclease V. Each of 9 lots of enzyme and positive and negative controls were incubated for 30 min, 18 hrs, 1 week or 2 weeks at 25° C. with either the A1 or C1 peptide (concentration of reporter peptide in the test solution=0.04 mg/ml). Protease activity was detected as altered mobility of the peptide in agarose gel electrophoresis. Each gel was photographed under fluorescent recording conditions. The migration of the intact peptide and cleaved fragments (designated as the F1 or F2 fragment) are noted. The percent of degraded peptide was calculated by conventional image analysis and is also recorded in FIG. 2.

Under these conditions, no protease activity was detected in 9 lots of T4 endonuclease V assayed at 30 minutes or even up to 18 hours (FIG. 2). The incubations of the enzyme samples with the substrates were then extended to 1 or 2 weeks. Even at this time, the A1 peptide did not consistently reveal substantial protease activity. However, the C1 peptide did reveal protease activity in the lots of T4 endo V (FIG. 2).

EXAMPLE 3

Two lots of T4 endo V were prepared from the same gel filtration process intermediate but were split into two parts based on elution from the column and were designated Lot I which was the central portion of the elution peak and Lot H which was a combination of the flanking fractions of the elution peak.

Figure 3:
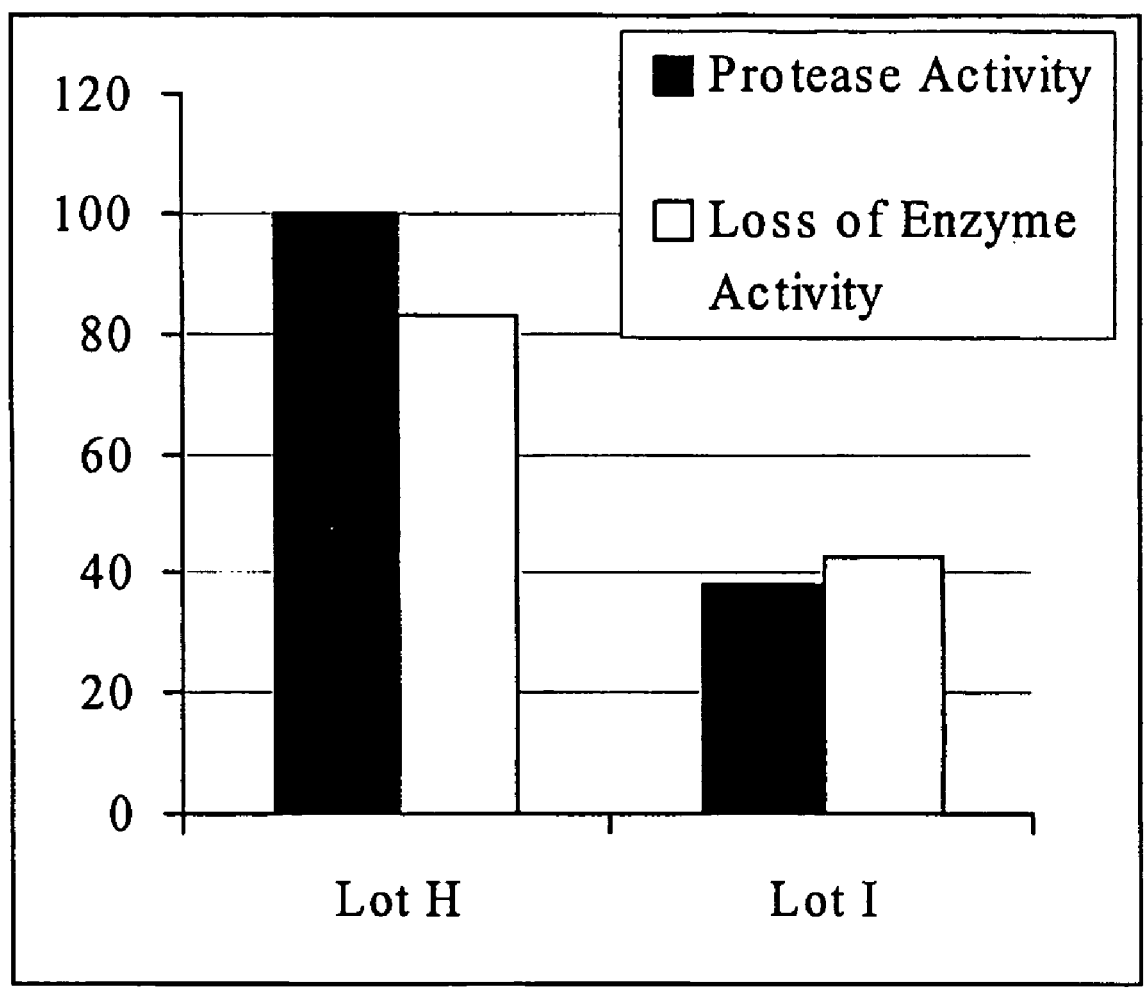
FIG. 3 shows the relationship of protease activity to stability of T4 endonuclease V. Two lots of T4 endonuclease V, with differing relative levels of protease activity (100% for Lot H; 38% for Lot I), were compared for the percentage of T4 endonuclease V activity lost at 14° C. after 5 days, as detected by activity assay (81% for Lot H; 41% for Lot I). The two lots differed in that Lot I was prepared from the central portion of the single-stranded DNA elution peak, and Lot H was prepared from the flanking portions of this central portion of the elution peak. The protease activity was determined using the C1 peptide at a concentration of 0.06 mg/ml in the test solution.

The lots were compared for protease activity as described in Example 2, and for the loss of enzyme activity, defined as the percent of enzyme activity lost in three weeks at 25° C. as described in Example 1. As shown in FIG. 3, Lot H had much higher protease activity and concomitantly much greater loss of enzyme activity. Lot I had much lower protease activity and a concomitantly lower loss of enzyme activity. However, this loss of enzyme activity was still too great to allow for non-refrigerated storage. This figure also suggests the source of the inconsistency in T4 endo V enzyme lots. Since the protease activity is higher in the flanking regions, the total amount of protease activity is dependent on the amount that is collected on either side of the center of the elution peak. Thus, very similar preparations may have different stability depending on very small variations in the amount of flanking regions included in the collected elution.

EXAMPLE 4

Figure 4:
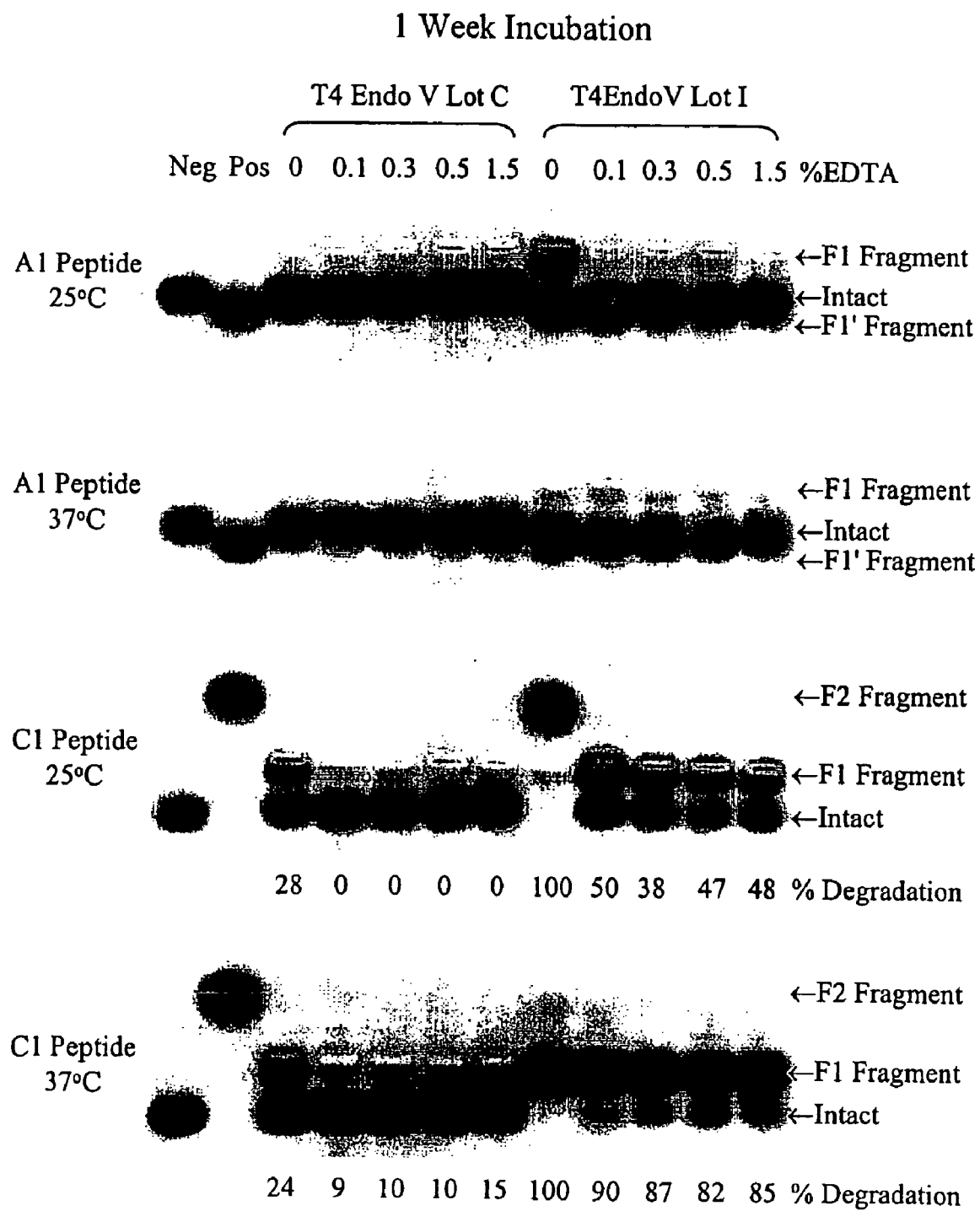
FIG. 4 shows partial inhibition of protease activity by EDTA. Two lots of T4 endo V, Lot C and Lot I, were tested for protease activity without and with increasing concentrations of EDTA. Neither preparation showed protease activity when tested with the A1 peptide at a concentration of 0.06 mg/ml in the test solution. Assays using the C1 peptide at the same concentration revealed that Lot C had a lower level of protease activity than Lot I, and that this was completely inhibited by the addition of EDTA. Lot I had greater protease activity that was also partially inhibited by EDTA.

This example illustrates the use of ethylenediaminetetracetic acid (EDTA) to inhibit protease activity in preparations of T4 endo V. Two lots were selected with high and low protease activity (FIG. 4). In a 7-day incubation assay for protease activity (see Example 2), Lot C degraded only 28% of the C1 peptide at 25° C., while Lot I degraded 100% of the peptide. Addition of 0.1% to 1.5% (w/v) EDTA significantly reduced the protease activity in Lot C, while 0.1% to 1.5% EDTA only reduced the cleavage of the C1 peptide by about 50% in Lot I. The A1 peptide did not reveal this finding (FIG. 4) since it did not consistently exhibit substantial degradation by the protease or proteases of the T4 endo V solution.

EXAMPLE 5

This example illustrates the use of anion exchange chromatography to remove protease activity during enzyme purification. Fast-flow Q-SEPHAROSE (BIORAD, Richmond, Calif.) was packed in a 1-liter cylindrical liquid chromatography column and equilibrated with phosphate buffered saline, pH 7.8. Two hundred ml of cell lysate containing T4 endonuclease V was divided into two parts and each part was passed over the FFQS column and the flow through was collected. The column was cleaned with high salt and 1 M NaOH between passages.

Figure 5:
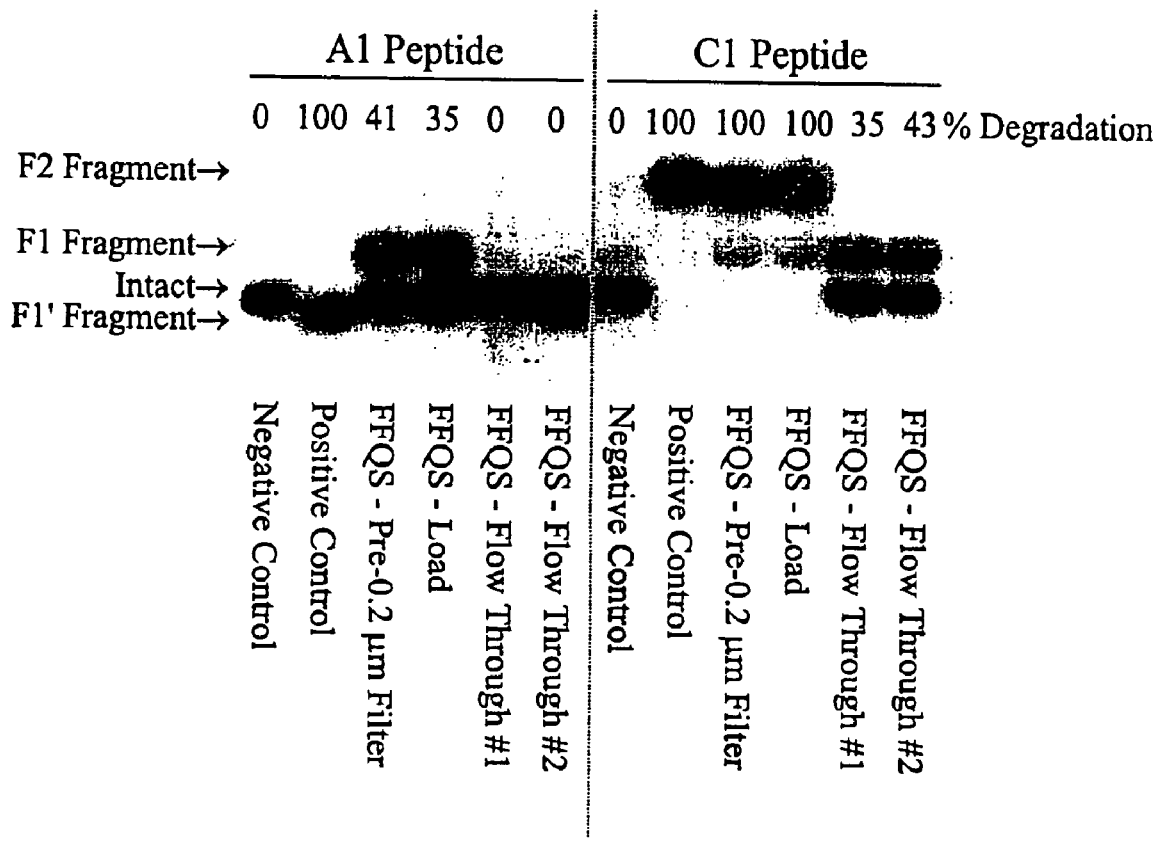
FIG. 5 shows partial removal of protease activity by fast-flow Q-SEPHAROSE (FFQS). Crude T4 endonuclease V lysate was passed over a column of Q-SEPHAROSE, and the protease activity was compared using both the A1 and C1 peptides incubated for 24 hrs with the concentration of reporter peptide in the test solution in each case being 0.04 mg/ml. Prior to application to the column, the preparation had protease activity against either peptide. After flow-through, the levels of protease activity were greatly reduced.

FIG. 5 shows that the protease activity was substantially reduced by this treatment, in a protease assay of 24 h. The lysates contained protease activity both before filtration (FFQS-Pre-0.21 µm filtration) and after filtration just prior to loading the column (FFQS-Load). However, the flow-through fractions, which contained the enzyme activity, showed greatly reduced protease activity, i.e., the proteases remained bound to FFQS. This was observed with both the A1 and the C1 peptide. Both these reporter peptides were able to detect protease activity because of the impure state of the lysate and the high concentrations of protein. For the same reasons, a 24 hour incubation revealed the protease activity.

EXAMPLE 6

This example demonstrates that the combination of removing proteases by Q-SEPHAROSE and inhibiting residual proteases using EDTA results in a pure enzyme preparation with virtually no protease activity.

A lot of T4 endonuclease V was prepared using the method described in U.S. Pat. No. 5,077,211 and also included two additional treatment steps, namely, a Q-SEPHAROSE treatment step after cell lysis and addition of 3.4 mM EDTA during subsequent purification steps.

Two pools of material eluting from the single-stranded DNA column of the basic purification process were collected. Each was assayed for protease activity (FIG. 6) for 7 days at either 25° or 37° C. While the reference standard Lot I showed degradation of the C1 substrate, the two batches of T4 endonuclease resulting from the method of the invention that included EDTA and Q-SEPHAROSE treatments revealed little degradation of the peptide.

EXAMPLE 7

Figure 7:
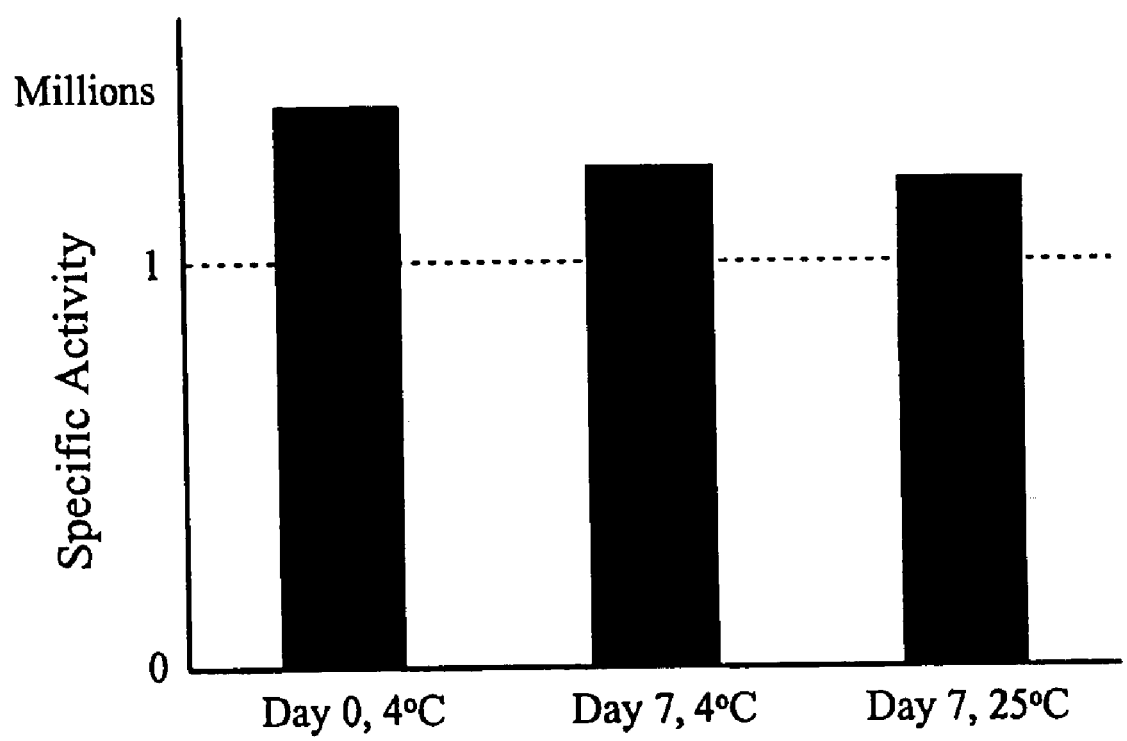
FIG. 7 shows stability at 25° C. with protease removal. A lot of T4 endonuclease V (Lot K) prepared using both protease removal by FFQS and inhibition by EDTA, was assayed for stability at one week at refrigeration (4° C.) and at room temperature (25° C.). No difference was detected in the specific activity of the stored enzyme at these two temperatures ($p>0.05$).
Figure 8:
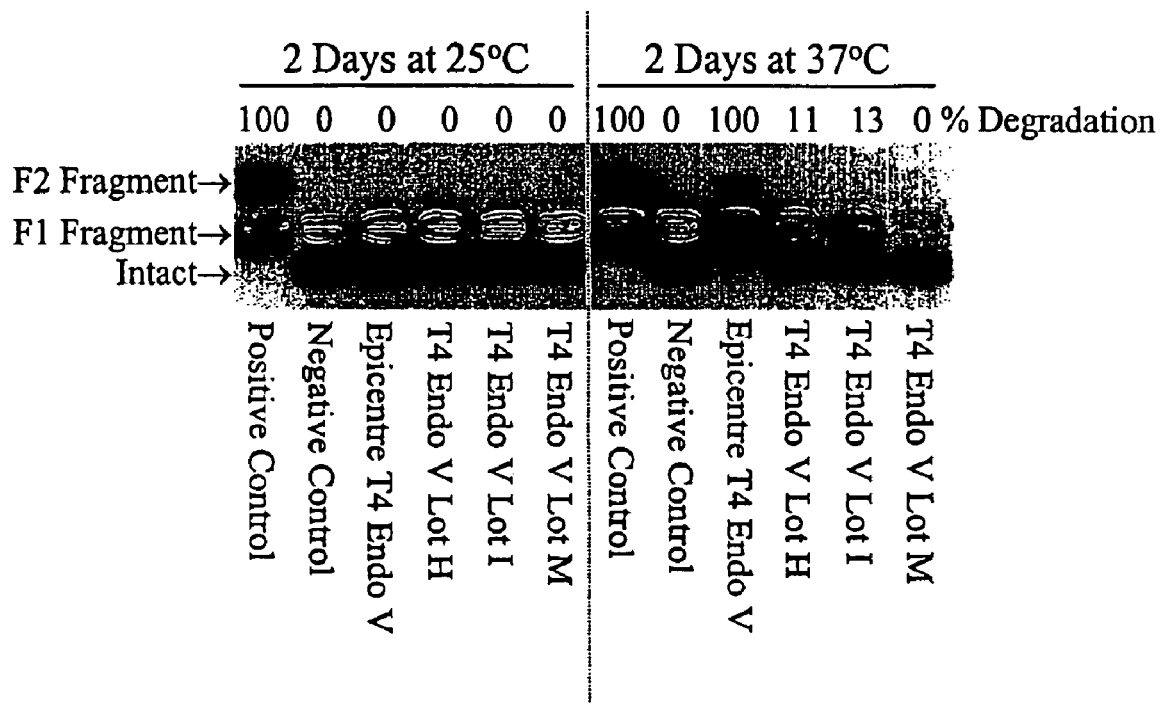
FIG. 8 shows that T4 endo V (Lot M) prepared with inclusion of 3.4 mM EDTA and passage over a column of Q-SEPHAROSE contained substantially less protease than batches made without EDTA or Q-SEPHAROSE (Lot H & I), or a commercially available batch of T4 endo V from EPICENTRE (Madison, Wis.). The protease assay was done by incubating test materials with C1 peptide at 25° C. and 37° C. for 2 days. The concentration of C1 peptide in the test solution was 0.03 mg/ml.

A lot of T4 endo V (Lot K) was prepared using the techniques of Example 6. The final product was then tested for stability at room temperature (25° C.) versus stability at refrigeration (4° C.). No difference in the specific activity of the protein, determined by statistical analysis, could be found after storage for 7 days (see FIG. 7).

Another lot of T4 endo V (Lot L) was prepared using the same method, and the final product was compared to T4 endo V prepared without removal/inhibition of proteases (Lot G of FIG. 2). The enzymes were held at 25° C. and assayed at the times indicated in Table 1. The activity at each time point was compared to the activity at the start. No T4 endo V activity was detected in the preparation with proteases after 1 week of incubation, i.e., Lot G of FIG. 2. In the protease-reduced preparation, T4 endo V activity was reduced but measurable after the first week, and no further activity was lost over the course of the next 3 weeks.

EXAMPLE 8

A Lot of T4 endo V (Lot M) was prepared using the techniques of Example 6 including passage of extracts over a column of Q-SEPHAROSE and the inclusion of 3.4 mM EDTA throughout the purification process. T4 endo V Lots H and I were prepared without Q-SEPHAROSE or EDTA. A commercially produced sample of T4 endo V was obtained from EPICENTRE (Madison, Wis.). These samples were then tested for protease activity during incubation with C1 peptide substrate for 2 days at 25° C. and 37° C. (see FIG. 8). Because of the low concentration of T4 endo V supplied by EPICENTRE, the enzyme concentration in the assay for the EPICENTRE preparation was about one-tenth that specified above for the preferred protease assays of the present invention. When tested at 37° C., T4 endo V Lot M made with EDTA and Q-SEPHAROSE contained no detectable protease. In contrast, under these same conditions, T4 endo V Lots H and I made without EDTA and Q-SEPHAROSE contained low but clearly detectable protease activity, and the commercially available batch of T4 endo V from EPICENTRE contained very high levels of protease activity. No protease activity was detectable when samples were tested at 25° C. for a 2 day incubation.

Although preferred and other embodiments of the invention have been described herein, further embodiments may be perceived by those skilled in the art without departing from the scope of the invention as defined by the following claims.

TABLE 1

Comparison of stability of T4 endonuclease V prepared by the method of the prior art (With Protease) compared to the present invention (Reduced Protease).

| Enzyme | Lot | Weeks at 25° C. | Percent Activity |
|---|---|---|---|
| With Protease | G | 0 | 100 |
| | | 1 | 0 |
| | | 2 | 0 |
| Reduced Protease | L | 0 | 100 |
| | | 1 | 23 |
| | | 4 | 28 |

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence:
      sequence is that of the C1 peptide of
      PROMEGA'S PEPTAG Protease Assay

<400> SEQUENCE: 1

Pro Leu Ser Arg Thr Leu Ser Val Ala Ala Lys
1               5                   10
```

What is claimed is:

1. A method for detecting protease contaminants in a T4 endonuclease V composition comprising:
   (i) preparing a test solution comprising an aqueous buffer, a sample of the T4 endonuclease V composition, and a labeled reporter peptide whose amino acid sequence is Pro Leu Ser Arg Thr Leu Ser Val Ala Ala Lys (SEQ ID NO:1);
   (ii) incubating the test solution at 25° C. for a period of at least 7 days; and
   (iii) determining the percentage of degraded reporter peptide after step (ii).

2. The method of claim 1 wherein the concentration of the T4 endonuclease V in the test solution is 0.095±0.05 mg/ml.

3. The method of claim 2 wherein step (ii) is performed for 7 days and step (iii) is performed by subjecting at least a portion of the test solution to a peptide separation procedure and determining said percentage of degraded reporter peptide by densitometry.

4. A method for preparing a T4 endonuclease V composition comprising:
   (A) providing an aqueous solution containing T4 endonuclease V; and
   (B) treating the aqueous solution so as to reduce the protease activity of the composition;
   wherein as a result of step (B), a sample of the aqueous solution when tested in accordance with claim 3 gives a percentage of degraded reporter peptide of less than 10 percent.

5. The method of claim 4 wherein in step (B), the aqueous solution is treated with a quaternary ammonium moiety attached to a solid support.

6. The method of claim 4 wherein in step (B), the aqueous solution is treated with a chelating agent.

7. The method of claim 4 wherein in step (B), the aqueous solution is treated with a quaternary ammonium moiety attached to a solid support and with a chelating agent.

8. The method of claim 4 comprising the additional step of storing the composition at a temperature above refrigeration and below 30° C. for a period of six months.

9. A composition of T4 endonuclease V prepared by the method of claim 4, 5, 6, or 7.

10. The method of claim 1 wherein step (ii) is performed for 7 days and step (iii) is performed by subjecting at least a portion of the test solution to a peptide separation procedure and determining said percentage of degraded reporter peptide by densitometry.

* * * * *